United States Patent
Rautschek et al.

(10) Patent No.: US 9,814,667 B2
(45) Date of Patent: *Nov. 14, 2017

(54) METHOD FOR PRODUCING SILICONE EMULSIONS

(71) Applicant: Wacker Chemie AG, Munich (DE)

(72) Inventors: Holger Rautschek, Nuenchritz (DE); Marco Kauschke, Glaubitz (DE)

(73) Assignee: WACKER CHEMIE AG, Munich (DE)

( * ) Notice: Subject to any disclaimer, the term of this patent is extended or adjusted under 35 U.S.C. 154(b) by 264 days.

This patent is subject to a terminal disclaimer.

(21) Appl. No.: 14/417,961

(22) PCT Filed: Aug. 8, 2013

(86) PCT No.: PCT/EP2013/066598
§ 371 (c)(1),
(2) Date: Jan. 28, 2015

(87) PCT Pub. No.: WO2014/026900
PCT Pub. Date: Feb. 20, 2014

(65) Prior Publication Data
US 2015/0174049 A1    Jun. 25, 2015

(30) Foreign Application Priority Data
Aug. 14, 2012 (DE) .................. 10 2012 214 429

(51) Int. Cl.
| | | |
|---|---|---|
| *A61K 8/89* | (2006.01) | |
| *C08G 77/06* | (2006.01) | |
| *A61K 8/891* | (2006.01) | |
| *C08L 83/04* | (2006.01) | |
| *A61K 8/55* | (2006.01) | |
| *A61Q 5/02* | (2006.01) | |
| *A61K 8/86* | (2006.01) | |
| *A61K 8/892* | (2006.01) | |
| *A61K 8/06* | (2006.01) | |
| *C08G 77/16* | (2006.01) | |
| *A61K 8/37* | (2006.01) | |
| *A61Q 5/12* | (2006.01) | |
| *C08K 5/521* | (2006.01) | |

(52) U.S. Cl.
CPC .............. *A61K 8/891* (2013.01); *A61K 8/06* (2013.01); *A61K 8/37* (2013.01); *A61K 8/55* (2013.01); *A61K 8/86* (2013.01); *A61K 8/892* (2013.01); *A61Q 5/02* (2013.01); *A61Q 5/12* (2013.01); *C08G 77/16* (2013.01); *C08L 83/04* (2013.01); *A61K 2800/21* (2013.01); *A61K 2800/805* (2013.01); *C08K 5/521* (2013.01)

(58) Field of Classification Search
CPC . A61K 8/891; A61K 8/37; A61K 8/06; A61K 8/55

See application file for complete search history.

(56) References Cited

U.S. PATENT DOCUMENTS

| | | |
|---|---|---|
| 3,294,725 A | 12/1966 | Findlay et al. |
| 3,706,695 A | 12/1972 | Huebner et al. |
| 4,194,988 A * | 3/1980 | Schneider .......... C08J 3/07 106/287.16 |
| 4,476,282 A | 10/1984 | Koerner et al. |
| 8,475,777 B2 | 7/2013 | Rautschek |
| 8,729,183 B2 | 5/2014 | Rautschek et al. |

FOREIGN PATENT DOCUMENTS

| | | |
|---|---|---|
| DE | 1595535 | 2/1970 |
| DE | 102009029520 A1 | 3/2011 |
| DE | 102011002668 A1 | 7/2012 |
| EP | 0093310 A2 | 11/1983 |
| EP | 1072629 A3 | 10/2002 |
| WO | 2006102010 A1 | 9/2006 |

OTHER PUBLICATIONS

X. Guo et al., "Calculation of hydrophile-lipophile balance for polyethoxylated surfactants by group contribution method", Journal of Colloid and Interface Science 298, 2006, pp. 441-450.

* cited by examiner

Primary Examiner — Lakshmi Channavajjala
(74) Attorney, Agent, or Firm — Brooks Kushman P.C.

(57) ABSTRACT

A method for producing aqueous silicone emulsions containing highly viscous polyorganosiloxanes having a low content of cyclic siloxanes in several steps; the addition of acidic compounds intended to catalyze polycondensation of the polyorganosiloxanes being carried out only after an emulsion is produced in the first step exclusively with nonionogenic emulsifiers, without impairing the rate of the polycondensation reaction.

17 Claims, No Drawings

METHOD FOR PRODUCING SILICONE EMULSIONS

CROSS-REFERENCE TO RELATED APPLICATIONS

This application is the U.S. National Phase of PCT Appln. No. PCT/EP2013/066598 filed Aug. 8, 2013, which claims priority to German application DE 10 2012 214 429.3 filed Aug. 14, 2012, the disclosures of which are incorporated in their entirety by reference herein.

BACKGROUND OF THE INVENTION

Field of the Invention

The invention relates to a method for producing aqueous silicone emulsions which contain high-viscosity polyorganosiloxanes and have a particularly low content of cyclic siloxanes, and to the use thereof.

Silicones have a variety of uses. To facilitate application and metering, particularly in the case of viscous products, it is desirable for many applications that the organosilicone compounds are in dilute form. Although the use of organic solvents such as benzene or hydrochlorocarbons is possible for this purpose, it is disadvantageous from an ecological and occupational health point of view. Consequently, the use takes place in most cases in form of aqueous emulsions or dispersions, usually as oil-in-water emulsions (O/W emulsions) which can be diluted with water. The oil phase is understood as meaning the water-immiscible organosilicone compounds, optionally dissolved in organic solvents.

For many applications, it is advantageous if the silicone has a high molecular weight and thus high viscosity. A known way of arriving at emulsions comprising a high-molecular-weight silicone is the emulsion polymerization of linear oligomers with terminal silanol groups. These oligomers are used, in the presence of interface-active condensation catalysts and a very small amount of water, to form a paste in which the polycondensation takes place before the actual emulsifying process is complete. Then, the emulsifying process is terminated by diluting this paste to the desired concentration (EP 93 310 B2; and its US equivalent U.S. Pat. No. 4,476,282, the disclosures of which are incorporated in their entirety by reference herein). However, volatile cyclic siloxanes are formed as an undesired by-product in the process. A reduction in the fraction of these volatile siloxanes can take place e.g. by firstly preparing an emulsion from the salt form of the anionic emulsifier/catalyst and then activating this by adding acid (EP-A 1 072 629; and its US equivalent U.S. Pat. No. 6,232,396, the disclosures of which are incorporated in their entirety by reference herein). This ultimately increases the salt fraction in the emulsion, which is disadvantageous for stability of the emulsion.

Special emulsifiers based on taurocholates likewise contribute to the reduction in the amount of cyclene which are formed in the emulsion condensation of siloxane oligomers (WO 2006 102 010; and its US equivalent US 2008/182833, the disclosures of which are incorporated in their entirety by reference herein). However, as the working examples clearly show, more than 1% octamethylcyclotetrasiloxane is also formed.

A considerable reduction in the fraction of newly formed cyclic siloxanes is possible if acidic alkyl phosphates are used as the emulsifiers catalyzing the emulsion condensation (DE 102 009 029 520 A1; and its US equivalent U.S. Pat. No. 8,475,777, the disclosures of which are incorporated in their entirety by reference herein).

A common feature of the methods according to the prior art is that the anionic emulsifier which catalyzes the emulsion polymerization has to be already added during the emulsion production. The fact that the catalyst also acts as an emulsifier has proven to be an advantage according to the prior art (DE-A 1595535; and its US equivalents U.S. Pat. No. 3,624,055 and U.S. Pat. No. 3,294,725, the disclosures of which are incorporated in their entirety by reference herein). On the contrary, in order not to delay or hinder the emulsion polymerization, it is proposed that the emulsion is produced using a sulfonic acid, and a nonionogenic emulsifier is only added after the emulsion polymerization has finished (U.S. Pat. No. 3,706,695).

On the other hand, emulsions of this kind are often produced in practice in such a way that either several batches are produced discontinuously and are transferred to a ripening tank, or a continuous campaign is produced over a certain time period in a ripening tank, where, after reaching the desired viscosity, the reaction is then stopped by neutralization. Additionally, during the emulsion production, mechanical energy is introduced into the emulsion by homogenization apparatuses, which ultimately leads to a temperature increase and increased cyclene formation. It is unavoidable that a not inconsiderable fraction of the emulsion resides in the tank for longer than required, as a result of which a fraction of cyclic oligomers can exceed the tolerable extent. Consequently, there is a need for an improved method to achieve the desired product properties, in particular a low content of cyclic siloxanes, with greater certainty.

SUMMARY OF THE INVENTION

It has now been unexpectedly and surprisingly discovered that aqueous silicone emulsions containing highly viscous polyorganosiloxanes and having a low content of cyclic siloxanes can be successfully prepared in several steps. Specifically, the addition of acidic compounds intended to catalyse polycondensation of the polyorganosiloxanes is carried out only after the emulsion is produced in the first step. The emulsion production can take place exclusively with nonionogenic emulsifiers, without impairing the rate of the polycondensation reaction.

DESCRIPTION OF THE PREFERRED EMBODIMENTS

The invention provides a method for producing emulsions of organic polysiloxanes, wherein
In a First Step:
(a) polyorganosiloxanes containing units of the general formula $$R^2_a(R^1O)_b SiO_{(4-a-b)/2} \qquad (I),$$

in which
$R^2$ each can be identical or different monovalent, optionally substituted hydrocarbon radical having 1 to 30 carbon atoms or hydrogen atom,
$R^1$ each can be identical or different hydrogen or a monovalent, optionally substituted hydrocarbon radical,
a is 0, 1, 2 or 3 and
b is 0, 1, 2 or 3,
with the proviso that the sum $a+b \leq 3$ and the organopolysiloxanes contain 5 to 500 units of the formula (I), and in at least one unit b is other than 0, (b) nonionogenic emulsifiers,
(c) water and
optionally
(d) further substances
are mixed by stirring and/or homogenization,
In a Second Step:
(e) acidic surface-active compounds of the general formula $$(RO)_nP(O)(OH)_{(3-n)} \tag{II}$$

in which
R each can be identical or different monovalent hydrocarbon radical having 4 to 30 carbon atoms and
n is 1 or 2,
are added to the emulsion at a temperature below 30° C., preferably at below 20° C., more preferably at below 10° C., to which the emulsion obtained in the first step must be cooled, if necessary, and the polyorganosiloxanes (a) are left to condense until the desired viscosity is reached and
In a Third Step:
the mixture obtained in the second step is admixed with base (f), such that the pH of the emulsion is greater than 5, and optionally water (c) and/or further substances (d) are added.

The pH is measured using an electrode in accordance with the US Pharmacopeia USP 33 at 20° C.

Suitable mixing and homogenizing tools which can be used in the method are all emulsifying devices known to the person skilled in the art such as high-speed stirrers, solvent disks, rotor-stator homogenizers, ultrasound homogenizers, and high-pressure homogenizers of various designs. If large particles are desired, low-speed stirrers are also suitable.

The method can be operated continuously, semicontinuously, or discontinuously.

The polyorganosiloxanes (a) are preferably those comprising units of the formula (I), more preferably those of units of the formula (I) with an average value of a from 1.90 to 2.05 and an average value of b from 0.001 to 0.2, in particular those of units of the formula (I), where $R^1$ is hydrogen atom, $R^2$ is the methyl radical and an average value of a from 1.990 to 2.005 and an average value of b from 0.01 to 0.1. Most preferably, the polyorganosiloxanes (a) are dimethylpolysiloxanes which carry dimethylhydroxysiloxy end groups.

Examples of hydrocarbon radicals $R^2$ are alkyl radicals such as the methyl, ethyl, n-propyl, isopropyl, 1-n-butyl, 2-n-butyl, isobutyl, tert-butyl, n-pentyl, isopentyl, neopentyl, tert-pentyl radical; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl radical and methyl cyclohexyl radical; alkenyl radicals such as the vinyl, 1-propenyl and the 2-propenyl radical; aryl radicals such as the phenyl, naphthyl, anthryl and phenanthryl radical; alkaryl radicals such as o-, m-, p-tolyl radical; xylyl radicals and ethylphenyl radicals; and aralkyl radicals such as the benzyl radical, the α- and the β-phenylethyl radical.

Examples of substituted radicals $R^2$ are radicals substituted with halogen, cyano, glycidoxy, polyalkylene glycol or amino groups such as trifluoropropyl, cyanoethyl, glycidoxypropyl, polyalkylene glycolpropyl, aminopropyl, or aminoethylaminopropyl radicals.

Preferably, in the units of the formula (I), at most one radical $R^2$ is hydrogen. Preferably, radical $R^2$ represents hydrocarbon radicals having 1 to 18 carbon atoms, more preferably the methyl or the phenyl radical, where in particular more than 80 mol % of the radicals $R^2$ in the siloxane (a) are methyl radicals.

Examples of radicals $R^1$ are the examples given for radicals $R^2$. Preferably, radical $R^1$ represents hydrogen and hydrocarbon radicals having 1 to 4 carbon atoms, more preferably hydrogen.

In formula (I), preferably, the sum a+b has a value of on average 1.5 to 2.4, more preferably on average 1.9 to 2.3, most preferably on average 1.95 to 2.1.

The siloxanes (a) used in the first step of the method consist preferably of 5 to 500, more preferably of 10 to 200, most preferably of 20 to 100, units of the formula (I).

Preferably, B is not 0 in 0.4 to 40% of the units of the formula (I) of the siloxanes (a) used in the first step of the method, more preferably in 2 to 10% of the units.

Examples of siloxanes (a) are polydiorganosiloxanes terminated with alkoxy or hydroxy groups, in particular polydiethylsiloxanes and polydimethylsiloxanes.

The siloxanes (a) used in the first step of the method have a viscosity of preferably 5 to 10,000 mm²/s, more preferably 10 to 500 mm²/s, in particular 30 to 100 mm²/s, in each case at 25° C.

Preferably, the siloxanes (a) are those of the formula $$HO[SiR^2_2O]_c\text{---}H \tag{III},$$

where $R^2$ has one of the aforementioned meanings, in particular the methyl radical, and c has a value from 5 to 500, preferably from 10 to 200, more preferably from 20 to 100.

The polysiloxanes (a) are standard commercial products and/or can be produced by known methods.

The nonionogenic emulsifiers be any desired emulsifiers known hitherto.

In the first step of the, emulsifiers (b) are used in amounts of preferably 1 to 40 parts by weight, more preferably 5 to 30 parts by weight, in each case based on 100 parts by weight of component (a).

Preferably, the nonionogenic emulsifiers (b) used are those which are selected from
(b1) ethoxylated triglycerides having 40 to 400 ethylene glycol groups,
(b2) ethoxylated sorbitan esters of fatty acids having 12 to 18 carbon atoms and 10 to 40 ethylene glycol groups,
(b3) compounds of the formula $$R^3\text{---}O\text{---}(CH_2CH_2O)_m\text{---}H \tag{IV}$$

and
(b4) compounds of the formula $$R^4CH_2C(O)\text{---}O\text{---}(CH_2CH_2O)_p\text{---}H \tag{V},$$

in which
$R^3$ is an alkyl radical having 10 to 30 carbon atoms,
$R^4$ is an alkyl radical having 10 to 30 carbon atoms,
m is a value from 5 to 100, and
p assumes a value from 5 to 100.

Examples of radicals $R^3$ and $R^4$ are, independently of one another, the n-decyl, n-dodecyl, n-tetradecyl, n-hexadecyl, n-octadecyl, and the n-octadecenyl radical.

Preferably, radical $R^3$ and $R^4$, independently of one another, are alkyl radicals having 12 to 20 carbon atoms, more preferably linear alkyl radicals. In particular, radical $R^3$ and $R^4$, independently of one another, are linear alkyl radicals having 12 to 20 carbon atoms and an even number of carbon atoms.

Preferably, m has a value from 10 to 40, more preferably from 20 to 40.

Preferably, p has a value from 10 to 50, more preferably from 20 to 50.

Examples of ethylated triglycerides having 40 to 400 ethylene glycol groups (b1) are ethoxylated castor oil having 200 ethylene glycol units, ethoxylated castor oil having 40 ethylene glycol units, and ethoxylated hydrogenated castor oil having 200 ethylene glycol units.

Examples of ethoxylated sorbitan esters of fatty acids having 12 to 18 carbon atoms and 10 to 40 ethylene glycol groups (b2) are polyoxyethylene (20) sorbitan stearate (polysorbate 60), polyoxyethylene (20) sorbitan tristearate (polysorbate 65), polyoxyethylene (20) sorbitan oleate (polysorbate 80), and polyoxyethylene(20) sorbitan laurate (polysorbate 20).

Examples of compounds (b3) of the formula (IV) are
i-$C_{13}H_{27}$—O—$(CH_2CH_2O)_{10}$—H,
$C_{18}H_{37}$—O—$(CH_2CH_2O)_{20}$—H,
$C_{18}H_{35}$—O—$(CH_2CH_2O)_{20}$—H and
$C_{12}H_{23}$—O—$(CH_2CH_2O)_{23}$—H.

Examples of compounds (b4) of the formula (V) are $C_{16}H_{33}$—$CH_2$—$C(O)$—O—$(CH_2CH_2O)_{20}$—H, $C_{16}H_{33}$—$CH_2$—$C(O)$—O—$(CH_2CH_2O)_{30}$—H, $C_{16}H_{33}$—$CH_2$—$C(O)$—O—$(CH_2CH_2O)_{40}$—H, and $C_{16}H_{33}$—$CH_2$—$C(O)$—O—$(CH_2CH_2O)_{100}$—H.

Preferably, the emulsifier (b) present in the emulsion has an HLB value greater than 14, more preferably greater than 15.5, in particular of 16.5 to 20. The HLB value is an expression of the equilibrium between hydrophilic groups and hydrophobic groups of an emulsifier. The definition of the HLB value and methods for its determination are known to the person skilled in the art and are described e.g. in Journal of Colloid and Interface Science 298 (2006) 441-450, and in the literature cited therein, especially citation [23].

Preferably, emulsifier (b) is a compound of the formula (IV).

Examples of radicals R in compound of the formula (II) are branched or unbranched alkyl radicals such as butyl, hexyl, 2-ethylhexyl, octyl, isononyl, n-decyl, dodecyl, isotridecyl, and n-tetradecyl radicals, unsaturated aliphatic radicals such as oleyl radicals, and also aromatic radicals such as phenyl, toloyl, xylyl, nonylphenyl, naphthyl, anthracyl, tristyrylphenyl, or benzyl radicals.

Preferably, radical R represents alkyl radicals having 4 to 18 carbon atoms, more preferably n-butyl, n-octyl, 2-ethylhexyl, n-decyl, n-dodecyl, or n-tetradecyl radicals, in particular n-octyl and n-decyl radicals.

Examples of compounds of the formula (II) are di-n-butyl phosphate, di-n-hexyl phosphate, mono-n-octyl phosphate, di-n-octyl phosphate, mono-2-ethylhexyl phosphate, di-2-ethylhexyl phosphate, mono-isononyl phosphate, di-isononyl phosphate, mono-n-decyl phosphate, n-octyl-n-decyl phosphate, di-n-decyl phosphate, monoisotridecyl phosphate, di-n-nonylphenyl phosphate, monooleyl phosphate, and distearyl phosphate. Preferably, the compounds of the formula (II) are mono-n-octyl phosphate, di-n-octyl phosphate, mono-n-decyl phosphate, n-octyl-n-decyl phosphate, and di-n-decyl phosphate. Preferably, the compounds of the formula (II) are mixtures of diesters and monoesters.

As a result of the production, the compounds used as components (e) can comprise so-called pyrophosphates, polyphosphates, or diphosphates, which do not correspond to the formula (II). In these compounds, two or more compounds of the formula (I) are joined together by P—O—P bridges. In the component (e), up to 50% of the phosphorus atoms can be present in this form, preferably less than 10% of the phosphorus atoms are present as pyrophosphates, more preferably less than 2%.

The acid number of the compound of the formula (II) is preferably in the range from 100 to 500, more preferably in the range from 200 to 400. The acid number of the compounds of the formula (II) is determined by their number of free OH groups and their molar mass, i.e. the amount of KOH in mg which is required to neutralize 1 g of compound of the formula (II).

Water (c) can be any type of water which has also been used hitherto for producing dispersions. The water (c) used is preferably partly or completely demineralized water, distilled or (repeatedly) redistilled water, water for medical or pharmaceutical purposes such as e.g. purified water (Aqua purificata according to Pharm. Eur.). Water (c) preferably has a conductivity of less than 50 µS/cm, more preferably less than 10 µS/cm, most preferably less than 1.3 µS/cm, in each case at 25° C. and 1010 hPa. In total, 50 to 1000 parts by weight of water, based on 100 parts by weight of components (a), are preferably used.

In addition to the components (a), (b), (c), (e), and (f), all further substances (d) which are usually added to silicone emulsions and are different than components (a), (b), (c), (e) and (f), can be used such as other siloxanes, silanes, in particular alkoxysilanes, further emulsifiers, thickeners, and/or protective colloids, and also additives such as preservatives, disinfectants, wetting agents, corrosion inhibitors, dyes, and fragrances. The addition of the components can however also take place after a subsequent method step, e.g. after the third step.

Examples of further siloxanes (d) are those of the formula (I), where b is 0, such as trimethylsiloxy-terminated polydimethylsiloxanes. Such siloxanes (d) are advantageously used to control the viscosity of the polysiloxane in the emulsion after the condensation reaction.

If further siloxanes (d) are used, the amounts are preferably 0.01 to 10 parts by weight, based on 100 parts by weight of component (a). Preference is given to using no further siloxanes (d).

Examples of further silanes (d) are methyltrimethoxysilane, tetraethoxysilane, vinyltriethoxysilane, or their hydrolysis/condensation products. Such silanes (d) are advantageously used to obtain branched or crosslinked siloxanes, e.g. those which form elastic films after drying of the emulsion. These silanes (d) can also be added after the third step.

If further silanes (d) are used, the amounts are preferably 0.01 to 10 parts by weight, based on 100 parts by weight of component (a).

Preferably, exclusively siloxanes containing units of the formula (I), in particular siloxanes of the formula (III), and no further siloxanes or silanes are used.

Examples of further emulsifiers (d) are other emulsifiers known to the person skilled in the art which are different than components (b) and (e), in particular alkali metal salts or amine salts of compounds of the formula (II).

It is also possible, but not preferred, to add some of the component (e) already in the first step, with the proviso that the pH of the emulsion obtained in the first step is greater than 3.5.

If thickeners and/or protective colloids are used as component (d), these are preferably acrylic acid copolymers.

If thickeners and/or protective colloids (d) are used, the amounts are preferably 0.01 to 2 parts by weight, based on 100 parts by weight of component (a). Preferably, no thickener and/or protective colloid (d) is used.

Examples of additives (d) are e.g. preservatives, dyes or fragrances known to the person skilled in the art, in particular preservatives such as methylisothiozolinone methylisothiazolinone, chloromethylisothiazolinone, benzylisothiazolinone, phenoxyethanol, methylparaben, ethylparaben, propylparaben, butylparaben, isobutylparaben, alkali metal benzoates, alkali metal sorbates, iodopropynyl butylcarbamate, benzyl alcohol, and 2-bromo-2-nitropropane-1,3-diol.

If additives (d) are used, the amounts are preferably 0.0005 to 2 parts by weight, based on 100 parts by weight of component (a). Preference is given to using additives (d), in particular preservatives. Preservatives (d) are preferably added in the third step and not in the first step.

In the first step of the method, all of the components can be mixed together by stirring and/or homogenizing, e.g. in any desired order. The periphery speed of the stirrer and/or rotor-stator homogenizer is preferably greater than 5 m/s, more preferably greater than 10 m/s, most preferably 5 to 50 m/s.

The pH of the emulsion obtained in the first step of the method is preferably more than 3.5, in particular more than 4.5. Preferably, the pH of the emulsion obtained in the first step, however, is not greater than 9, in particular not greater than 8.

Preferably, the emulsion produced in the first step comprising components (a), (b), (c), and optionally (d) and (e) is produced in such a way that firstly some of the component (c) is mixed with the other components to give a high-viscosity and nonflowable paste. It is especially preferred if the yield point (corresponding to DIN 53019-1 and standards cited therein) of this pasty premix is greater than 100 Pa, in particular greater than 1000 Pa. Preferably, this pasty premix is then homogenized under the action of shear energy until the desired particle size is reached and diluted with water (c) with stirring and/or homogenization such that a flowable emulsion is formed which preferably comprises more than 50 parts by weight, more preferably 50 to 1000 parts by weight, in particular 80 to 500 parts by weight, of water, in each case based on 100 parts by weight of component (a).

In the first step, preferably no further components are used over and above the components (a), (b), and (c), and optionally (d), and (e).

Preferably, the first step is carried out at temperatures of 5 to 80° C., more preferably 10 to 50° C., and the pressure of the ambient atmosphere, i.e. between 900 and 1100 hPa. However, the first step can also be carried out at an increased pressure of up to 20,000 hPa, preferably of up to 10,000 hPa.

The mixture obtained in the first step has a particle size (median value of the volume distribution) of preferably less than 1 μm, more preferably less than 500 nm, more preferably 50 to 200 nm. The particle size can be determined with laser scattering or by laser diffraction in accordance with DIN ISO 13320.

In a specific variant of the method, particle sizes (average value of the volume distribution) greater than >1 μm are desired, in particular particle sizes of 5 to 50 μm, in which case the method is then preferably performed by mixing with a low shear force, e.g. simple stirring of the components.

The time required for carrying out the first step is preferably 5 minutes to 4 hours, more preferably 30 minutes to 3 hours, most preferably 1 to 2 hours.

In the second step, the mixture produced in the first step is mixed at a temperature of below 30° C. with the component (e), where the melting point of the mixture preferably forms the lower temperature limit.

If the temperature of the emulsion obtained in the first step is higher than below 30° C. required in the second step, the emulsion is cooled to the desired temperature in the second step before adding the component (e). This optionally carried out cooling preferably takes place by cooling via the container wall or a heat exchanger. All known heat exchangers can be used as cooling medium, e.g. water, cooling brine, or organic heat carriers such as Marlotherm®.

The addition of the component (e) takes place by simple stirring, a homogenization is possible, but in most cases is not necessary, and therefore not preferred. To facilitate metering, it is possible, but not preferred, to disperse component (e) in water (c).

The pH of the emulsion obtained in the second step is preferably less than 2.5, more preferably less than 2.0, most preferably 1.4 to 1.8.

The component (e) is added in amounts of preferably 1 to 40 parts by weight, more preferably 2 to 20 parts by weight, most preferably from 4 to 10 parts by weight, in each case based on 100 parts by weight of polysiloxane (a). The use amount can also be divided. Preferably, up to at most 40% by weight of the total use amount of (e) is added in the first step, and the remaining part is added in the second step. It may be advantageous to combine a small particle size with low cyclone contents if the amount added in the first step contributes to emulsion formation, but catalyzes reactions on the siloxane only to a small extent, if at all, in this phase of the method.

The total amount of component (e) is preferably used in the second step.

In the second step, preferably no further components are used over and above the components (e) and optionally (c).

Then, the polycondensation of the organopolysiloxanes (a) takes place until the desired viscosity is reached, i.e. a viscosity of preferably greater than 10,000 mm$^2$/s, more preferably greater than 100,000 mm$^2$/s, most preferably greater than 1,000,000 mm$^2$/s, in each case at 25° C., measured in accordance with DIN 53019.

Preferably, the duration of the condensation reaction after adding (e) in the second step is 1 to 200 hours, more preferably 8 to 96 hours, most preferably 12 to 72 hours.

The second step can take place in the same container as the first step. However, the emulsion can also be transferred to a special container, where several batches produced one after the other are optionally mixed for the second step. However, it is also possible to carry out the first step continuously and the second step in a ripening tank.

The alcohols optionally produced as condensation by-products, e.g. if $R^1$ in formula (I) is other than hydrogen atom, can remain in the emulsion or be removed, for example by distillation in vacuum or by extraction.

When carrying out the second step, the pressure is not important for the product quality. In practice, this step is carried out e.g. at atmospheric pressure, i.e. between 900 and 1100 hPa. The second step can also be carried out at an increased pressure of e.g. up to 20,000 hPa, in particular of up to 10,000 hPa, or at reduced pressure.

Examples of the bases (f) used in the third step are alkali metal hydroxides such as NaOH and KOH, and also amines such as monoethanolamine and triethanolamine, and salts of weak acids such as sodium citrate, sodium silicate, potassium acetate, or potassium phosphate.

Preferably, the bases (f) which are used in the third step are alkali metal or alkaline earth metal hydroxides, ammonia and amines, more preferably NaOH, KOH, monoethanolamine, and triethanolamine.

The pH of the emulsion after carrying out the third step is preferably 5 to 10, more preferably 6 to 8, most preferably about 7.

The third step is carried out at temperatures of preferably 2 to 30° C., more preferably 5 to 20° C., and atmospheric pressure, i.e. between 900 and 1100 hPa.

The emulsions can now optionally be mixed as desired with water (c) and/or further substances (d), in particular preservatives.

Preferably, no further components are used in addition to the components (a), (b), (c), (e), (f), and optionally (d).

The components can be in each case one type of such a component, or else a mixture of at least two types of a particular component.

The emulsions advantageously comprise no or only a very small fraction of cyclic siloxanes, in particular of octaorganylcyclotetrasiloxanes ($D_4$). The organyl groups in the cyclosiloxanes are governed by the organyl groups in the organopolysiloxane used and are preferably methyl groups.

The emulsions comprise preferably less than 0.2% by weight, more preferably less than 0.1% by weight, of octaorganylcyclotetrasiloxane, in particular octamethylcyclotetrasiloxane ($D_4$), in each case based on component (a) used.

The emulsions have a particle diameter of preferably 50 to 1000 nm, more preferably from 50 to 500 nm, most preferably form 50 to 200 nm. The data referring to the median value of the volume distribution is measured according to the principle of laser scattering or Fraunhofer diffraction (corresponding to ISO 13320).

The emulsions have a content of non-volatile fractions measured in accordance with DIN EN ISO 3251 of preferably 1 to 80% by weight, more preferably from 10 to 65% by weight, most preferably from 30 to 60% by weight.

Surprisingly, it has been found that it is possible to add the acidic compounds of the formula (II) which are intended to catalyze the polycondensation of the siloxanes (a) only after the emulsion production in the first step, which can take place e.g. exclusively with nonionogenic emulsifiers, without impairing the rate of the polycondensation reaction.

The emulsions have the advantage that they contain high-viscosity polydiorganosiloxanes and have a particularly low content of cyclene.

Furthermore, the emulsions have the advantage that they are very stable and therefore have a long shelf life.

The emulsions have the advantage that they are storage-stable and have excellent application properties such as a very good effect as a release agent and lubricant, a good wetting capacity on various substrates, a good conditioning effect in hair care products, i.e. significant reduction in the wet and dry combing force.

The method has the advantage that emulsions with high molecular weight siloxanes can be produced in a simple and cost-effective way.

The method also has the advantage that the fraction of cyclic siloxanes remains very low even after a prolonged duration of the third step, and this is especially favorable, e.g. in the case of a continuous production with a broader residence time range.

The method has the additional advantage that the viscosity of the oil can be varied within a wide range and can easily be adjusted without an increased fraction of cyclic siloxanes being formed.

The emulsions can be used for all purposes for which emulsions with high viscosity siloxanes have also hitherto been used, for example, as release agents, lubricants, hydrophobization agents and for textile impregnation, during the processing of rubber and plastics or during metal processing, for glass and mineral building materials or as a constituent of body care products.

In the examples below, all of the data with respect to parts and percentages relates, unless stated otherwise, to the weight. Unless stated otherwise, the examples which follow are carried out at atmospheric pressure, i.e. at about 1010 hPa, and at room temperature, thus about 25° C. or at a temperature which is established upon combining the reactants at room temperature without additional heating or cooling. All of the viscosity data listed in the examples refers to a temperature of 25° C.

The emulsions produced in the examples below were examined as follows:

The particle size was determined using a particle size analyzer Zetasizer ZEN1600/Nano-S, Malvern, Software Version 6.01 by dynamic light scattering. For this analysis, the emulsions were diluted to 0.5% with filtered and degassed water. In the case of the coarsely particulate emulsions, the particle size measurement was carried out using a Malvern Mastersizer X (Malvern Instruments GmbH D-Herrenberg; measurement principle: Fraunhofer diffraction corresponding to ISO 13320). The stated values for the particle size always refer to the medium value of the volume distribution D(50).

The measurement of the pH was carried out in accordance with the US Pharmacopeia USP 33 at 20° C.

To determine the oil viscosity, 20 g of emulsion were admixed with 30 g of acetone; in doing so, the emulsion separated. The acetone/water phase was separated off and the procedure was repeated once more. Then, the polymer was washed three times with water and dried at 110° C. with stirring until water droplets could no longer be seen. The polymer was then after-treated for a further 8 hours at 110° C. in a drying cabinet. The viscosity was determined in accordance with DIN 53019 using a cone-plate viscosimeter MCR 300 (Paar-Physika) at 25° C. and a shear gradient of 1/s.

To determine the content of octamethylcyclotetrasiloxane ($D_4$), 0.5 g of the sample were mixed with 10 ml of ultracure acetone which comprised 120 ppm of n-dodecane as internal standard. After shaking for a period of 16 hours, two phases were formed. 10 µl of the supernatant clear phase were injected into a gas chromatograph. A double determination was carried out. The content of octamethylcyclotetrasiloxane ($D_4$) in the emulsion was determined by reference to a calibration curve recorded beforehand. It was then possible to calculate the $D_4$ content based on the polysiloxane (a).

The test results of the examples listed below are summarized in table 1.

Example 1

100 parts of an α,ω-hydroxy-terminated polydimethylsiloxane with a viscosity of 60 mPas and a temperature of 20° C. were introduced as charge in a beaker. Using a rotor-stator homogenizer (Ultra-Turrax, peripheral speed 16 m/s), 14 parts of an ethoxylated lauryl alcohol of the formula $C_{12}H_{23}$—O—$(CH_2CH_2O)_{23}$—H (available under the name "Brij 35" from Croda GmbH, D-Nettetal) and 10 parts of water were added and homogenized for 10 min. The resulting gel-like paste (yield point 3210 Pa) with a particle size of less than 200 nm had a temperature of 48° C. This paste was diluted with 100 parts of water over the course of 10 min and cooled to 5° C. The pH was 5.5. Then, 6 parts of an octyl/decyl phosphate with an acid number of 295 mg KOH/g, i.e. which consists of approximately equal fractions of monoesters and diesters (available under the name "Crodafos 810 A" from Croda GmbH, D-Nettetal), were stirred in. The pH was 1.9. The emulsion was stored for 48 hours at 5° C. and then adjusted to a pH of 7 with triethanolamine, and 0.18 parts of preservative based on methylisothiazolinone were added in combination with ethylhexylglycerol (available under the name "Euxyl K220" from Schülke&Mayr GmbH, D-Norderstedt).

Example 2

100 parts of an α,ω-hydroxy-terminated polydimethylsiloxane with a viscosity of 60 mPas and a temperature of 20° C. were introduced as charge in a beaker. Using a rotor-stator homogenizer (Ultra-Turrax, peripheral speed 16 m/s), 22 parts of an ethoxylated lauryl alcohol of the formula $C_{12}H_{23}$—O—$(CH_2CH_2O)_{23}$—H (available under the name "Brij 35" from Croda GmbH, D-Nettetal) and 10 parts of water were added and homogenized for 10 min. The resulting gel-like paste (yield point 2840 Pa) with a particle size of less than 200 nm had a temperature of 42° C. The paste was diluted over the course of 10 min with 100 parts of water and cooled to 5° C. The pH was 5.5. Then, 10 parts of an octyl/decyl phosphate with an acid number of 295 mg KOH/g (available under the name "Crodafos 810 A" from Croda GmbH, D-Nettetal) were stirred in. The pH was 1.5. The emulsion was stored for 24 hours at 5° C. and then adjusted to a pH of 7 with triethanolamine, and 0.18 parts of preservative based on isothiazolinones (available under the name "Kathon CG" from Acima Chemical Industries Ltd. CH-9471 Buchs/SG, Switzerland) were added.

Example 3

100 parts of an α,ω-hydroxy-terminated polydimethylsiloxane with a viscosity of 60 mPas and a temperature of 20° C. were introduced as charge in a beaker. Using a rotor-stator homogenizer (Ultra-Turrax, peripheral speed 16 m/s), 14 parts of an ethoxylated lauryl alcohol of the formula $C_{12}H_{23}$—O—$(CH_2CH_2O)_{23}$—H (available under the name "Brij 35" from Croda GmbH, D-Nettetal), 5 parts of an octyl/decyl phosphate with an acid number of 295 mg KOH/g (available under the name "Crodafos 810 A" from Croda GmbH, D-Nettetal), 1.7 parts of triethanolamine and 10 parts of water were added and homogenized for 10 min. The resulting gel-like paste (yield point 1580 Pa) with a particle size of less than 200 nm had a temperature of 40° C. The paste was diluted over the course of 10 min with 100 parts of water and cooled to 5° C. The emulsion had a pH of 3.7. Then, a further 5 parts of an octyl/decyl phosphate with an acid number of 295 mg KOH/g (available under the name "Crodafos 810 A" from Croda GmbH, D-Nettetal) were stirred in. The pH was 2.3. The emulsion was stored for 48 hours at 5° C. and then adjusted to a pH of 7 with triethanolamine, and 0.18 parts of preservative based on methylisothiazolinone were added in combination with ethylhexylglycerol (available under the name "Euxyl K220" from Schülke&Mayr GmbH, D-Norderstedt).

Example 4

The procedure described in example 2 was repeated except that instead of octyl/decyl phosphate, 2-ethylhexyl phosphate with an acid number 300 mg KOH/g, i.e. which consists of approximately equal fractions of monoesters and diesters, was used, which is available under the name "Servoxyl VPTZ 100" from Elementis GmbH, D-Cologne.

Example 5

The procedure described in example 2 was repeated except that instead of octyl/decyl phosphate, isotridecyl phosphate with an acid number of 220 mg KOH/g, i.e. which consists of approximately equal fractions of monoesters and diesters, was used, which is available under the name "Servoxyl VPDZ 100" from Elementis GmbH, D-Cologne.

Comparative Example V1

100 parts of an α,ω-hydroxy-terminated polydimethylsiloxane with a viscosity of 60 mPas were introduced as charge in a beaker. Using a rotor-stator homogenizer (Ultra-Turrax, peripheral speed 16 m/s), 10 parts of an octyl/decyl phosphate with an acid number of 295 mg KOH/g (available under the name "Crodafos 810 A" from Croda GmbH, D-Nettetal), 14 parts of an ethoxylated lauryl alcohol of the formula $C_{12}H_{23}$—O—$(CH_2CH_2O)_{23}$—H (available under the name "Brij 35" from Croda GmbH, D-Nettetal) and 10 parts of water were added and homogenized for 10 min. The resulting gel-like paste (yield point 1940 Pa) with a particle size of less than 200 nm had a temperature of 23° C. The paste was diluted over the course of 10 min with 100 parts of water and stored at 5° C. The emulsion had a pH of 1.6. After 72 hours, the emulsion is adjusted to a pH of 7 with triethanolamine, and 0.18 parts of preservative based on methylisothiazolinone were added in combination with ethylhexylglycerol (available under the name "Euxyl K220" from Schülke&Mayr GmbH, D-Norderstedt).

Comparative Example V2

Comparative example V1 was repeated. However, the octyl/decyl phosphate was neutralized immediately with triethanolamine and, after cooling the emulsion to 5° C., acidified again with phosphoric acid.

After the condensation time had elapsed, the emulsion was neutralized afresh with triethanolamine. Then, the emulsion separated on account of the excessively high salt content within a few hours and could not be further used.

Comparative Example V3

Example 1 was repeated but the phosphoric acid ester was added at a temperature of 40° C., and the emulsion was stored for 48 hours at room temperature.

Comparative Example V4

Example 1 was repeated but instead of the phosphoric acid ester, 3% of an alkylbenzenesulfonic acid (available under the name Marlon AS 3 acid from SASOL AG D-Marl) was used.

TABLE 1

| Example | Particle size D(50) in nm | Oil viscosity in mm$^2$/s | $D_4$ in ppm[1] | $D_4$ in % by weight[2] |
|---|---|---|---|---|
| 1 | 175 | 1,190,000 | 228 | 0.054 |
| 2 | 82 | 930,000 | 380 | 0.090 |
| 3 | 112 | 1,810,000 | 490 | 0.117 |
| 4 | 87 | 1,490,000 | 330 | 0.079 |

TABLE 1-continued

| Example | Particle size D(50) in nm | Oil viscosity in mm²/s | $D_4$ in ppm[1] | $D_4$ in % by weight[2] |
|---|---|---|---|---|
| 5 | 94 | 669,000 | 270 | 0.064 |
| V1 | 97 | 1,780,000 | 1100 | 0.262 |
| V2 | Emulsion separated after neutralization | | | |
| V3 | 120 | 548,000 | 1550 | 0.369 |
| V4 | 142 | 1,140,000 | 2260 | 0.538 |

[1]based on the emulsion,
[2]based on siloxane

Surprisingly, the subsequent addition of the acid phosphate does not lead to a slower condensation reaction.

However, the formation of $D_4$ is considerably suppressed compared to the prior art. The stability of the emulsion in which, as is proposed in EP-A 1 072 629, the acidic anionic emulsifier is neutralized prior to the production of the emulsion and is then activated again by adding acid, was inadequate. Comparative example 3 shows that a process analogous to the method according to the invention with conventional emulsifiers leads to a significantly greater formation of $D_4$.

Example 6

Production of a Coarsely Particulate Emulsion 100 parts of an α,ω-hydroxy-terminated polydimethylsiloxane with a viscosity of 100 mPas were introduced as charge in a beaker at 25° C. Using a paddle stirrer, 14 parts of an ethoxylated lauryl alcohol of the formula $C_{12}H_{23}$—O—$(CH_2CH_2O)_{23}$—H (available under the name "Brij 35" from Croda GmbH, D-Nettetal) dissolved in 20 parts of water were added, and the mixture was stirred for 10 min. A further 40 parts of water were added stepwise.

Then, at a temperature of 5° C. 6 parts of an octyl/decyl phosphate with an acid number of 295 mg KOH/g (available under the name "Crodafos 810 A" from Croda GmbH, D-Nettetal) were stirred in. The pH was 1.6. The emulsion was stored for 48 hours at 5° C. and then adjusted to a pH of 7 with triethanolamine, and 0.18 parts of preservative based on methylisothiazolinone in combination with ethylhexylglycerol (available under the name "Euxyl K220" from Schülke&Mayr GmbH, D-Norderstedt) were added. The results of the test are summarized in table 2.

Comparative Example 5

Example 6 was repeated except that instead of the phosphoric acid ester, 3% of an alkylbenzenesulfonic acid (available under the name Marlon AS 3 acid from SASOL AG D-Marl) were used. The emulsion was stored for 72 hours at 5° C. and then neutralized.

TABLE 2

| Example | Particle size D(50) in μm | Oil viscosity in mm²/s | $D_4$ in ppm[1] | $D_4$ in % by weight[2] |
|---|---|---|---|---|
| 6 | 18 | 1,820,000 | 400 | 0.070 |
| V5 | 31 | 20,000 | 2810 | 0.493 |

[1]based on the emulsion,
[2]based on siloxane

Surprisingly, the coarsely particulate emulsion exhibits an efficient polycondensation and thus high oil viscosity for a very low content of $D_4$, whereas the comparative example already comprises a high fraction of $D_4$ without a very high oil viscosity appearing to have been reached.

Example 7

A shampoo is formulated as follows (the components are referred to in accordance with INCI-nomenclature):

0.2 parts of guar hydroxypropyltrimonium chloride (available under the name N-Hance® 3000 from Hercules Inc.) are dispersed in 11.92 parts of water. 71.7 parts of sodium laureth sulfate (available under the name Genapol LRO 26.5% from Clariant GmbH) are slowly stirred in and the mixture is heated to 75° C. During this step, 0.3 parts of PEG-150 distearate (available under the name Emulgin EO 33 from Cognis Deutschland GmbH) are added upon reaching 50° C., and when 65° C. is reached, 1.2 parts of glycol distearate (available under the name Genapol PMS from Clariant GmbH) are added. The mixture is mixed until 75° C. is reached. Then, the mixture is cooled. When 35° C. is reached, 0.6 parts of preserver Kathon CG (available from Acima Chemical Industries Ltd. Inc. CH-9471 Buchs) and 4 parts of the emulsion of example 2 are added, and the mixture is stirred for 5 minutes. Finally, 10.06 parts of Cocamidopropyl Betaine (available under the name Genagen CAB 30% from Clariant GmbH) and 0.56 parts of sodium chloride are added, and in each case stirring is performed for 10 minutes. This shampoo improves the ability to comb both the dry and the wet hair as well as the feel to the touch in wet and dry hair.

The invention claimed is:

1. A method for producing an emulsion of organopolysiloxanes, comprising the steps of:
    in a first step, mixing by stirring and/or homogenization
    (a) polyorganosiloxanes containing units of the formula $$R^2_a(R^1O)_b SiO_{(4-a-b)/2} \quad (I),$$

where
    $R^2$ each are identical or different monovalent, optionally substituted hydrocarbon radical having 1 to 30 carbon atoms or hydrogen,
    $R^1$ each are identical or different hydrogen or a monovalent, optionally substituted hydrocarbon radical,
    a is 0, 1, 2 or 3 and
    b is 0, 1, 2 or 3,
    with the proviso that the sum a+b≤3, the organopolysiloxanes contain 5 to 500 units of the formula (I), and b is other than 0 in at least one unit,
    (b) nonionogenic emulsifiers,
    (c) water, and
    optionally
    (d) further substances to obtain a flowable emulsion;
        in a second step, adding (e) acidic surface-active compounds of the formula $$(RO)_n P(O)(OH)_{(3-n)} \quad (II),$$

where
    R each are identical or different monovalent hydrocarbon radicals having 4 to 30 carbon atoms and
    n is 1 or 2,
    to the flowable emulsion at a temperature below 30° C., after optionally cooling the emulsion obtained in the first step to a temperature below 30° C., and condensing the polyorganosiloxanes (a) until a desired viscosity is reached, obtaining a mixture; and
        in a third step, mixing the mixture obtained in the second step with a base (f) so that a pH of a resulting emulsion is greater than 5, and optionally adding additional water (c) and/or further substances (d).

2. The method of claim 1, wherein the polyorganosiloxanes (a) have the formula $$HO[SiR^2_2O]_c\text{---}H \quad (III),$$

where
R$^2$ each are identical or different monovalent, optionally substituted hydrocarbon radicals having 1 to 30 carbon atoms or hydrogen and
c has a value from 5 to 500.

3. The method of claim 1, wherein the nonionogenic emulsifiers (b) are selected from the group consisting of
(b1) ethoxylated triglycerides having 40 to 400 ethylene glycol groups,
(b2) ethoxylated sorbitan esters of fatty acids having 12 to 18 carbon atoms and 10 to 40 ethylene glycol groups,
(b3) compounds of the formula $$R^3\text{---}O\text{---}(CH_2CH_2O)_m\text{---}H \quad (IV)$$

and
(b4) compounds of the formula $$R^4CH_2C(O)\text{---}O\text{---}(CH_2CH_2O)_p\text{---}H, \text{ and mixtures thereof,} \quad (V),$$

where
R$^3$ represents an alkyl radical having 10 to 30 carbon atoms,
R$^4$ represents an alkyl radical having 10 to 30 carbon atoms,
m has a value from 5 to 100 and
p has a value from 5 to 100.

4. The method of claim 1, wherein compounds of the formula (II) are mono-n-octyl phosphate, di-n-octyl phosphate, mono-n-decyl phosphate, n-octyl-n-decyl phosphate, or di-n-decyl phosphate.

5. The method of claim 1, wherein a pH of the emulsion obtained in the first step is more than 3.5.

6. The method of claim 1, wherein the second step is carried out at a temperature below 20° C.

7. The method of claim 1, wherein a pH of an emulsion obtained in the second step is less than 2.5.

8. The method of claim 1, wherein the base (f) is an alkali metal, an alkaline earth metal hydroxide, ammonia, an amine, or a blend thereof.

9. The method of claim 1, wherein the pH of the resulting emulsion after carrying out the third step is 5 to 10.

10. The method of claim 1, wherein a resulting emulsion contains less than 0.2% by weight of octaorganylcyclotetrasiloxane, based on the component (a).

11. The method of claim 1, wherein a resulting emulsion contains less than 0.1% by weight of octaorganylcyclotetrasiloxane, based on the component (a).

12. The method of claim 1, wherein the organopolysiloxanes obtained have a viscosity of >100,000 mm$^2$/s at 25° C., and a content of octaoganylcyclotetrasiloxane of less than 0.2% by weight relative to the weight of the organopolysiloxanes.

13. The method of claim 1, wherein the organopolysiloxanes obtained have a viscosity of >1,000,000 mm$^2$/s at 25° C., and a content of octaoganylcyclotetrasiloxane of less than 0.2% by weight relative to the weight of the organopolysiloxanes.

14. The method of claim 1, wherein the organopolysiloxanes obtained have a viscosity of >100,000 mm$^2$/s at 25° C., and a content of octaoganylcyclotetrasiloxane of less than 0.1% by weight relative to the weight of the organopolysiloxane.

15. The process of claim 1, wherein the amount of water (c) is from 50 to 1000 parts by weight relative to the weight of the polyorganosiloxanes of the formula I.

16. The process of claim 1, wherein the amount of water (c) is from 80 to 500 parts by weight relative to the weight of the polyorganosiloxanes of the formula I.

17. The process of claim 1, wherein the second step is carried out at a temperature below 10° C.

\* \* \* \* \*